(12) United States Patent
Ferree

(10) Patent No.: US 7,066,958 B2
(45) Date of Patent: Jun. 27, 2006

(54) PROSTHETIC COMPONENTS WITH PARTIALLY CONTAINED COMPRESSIBLE RESILIENT MEMBERS

(76) Inventor: Bret A. Ferree, 1238 Cliff Laine Dr., Cincinnati, OH (US) 45208

(*) Notice: Subject to any disclaimer, the term of this patent is extended or adjusted under 35 U.S.C. 154(b) by 0 days.

(21) Appl. No.: 10/434,930

(22) Filed: May 9, 2003

(65) Prior Publication Data

US 2004/0024460 A1 Feb. 5, 2004

Related U.S. Application Data

(63) Continuation-in-part of application No. 10/422,282, filed on Apr. 24, 2003.

(60) Provisional application No. 60/379,462, filed on May 10, 2002.

(51) Int. Cl.
*A61F 2/44* (2006.01)

(52) U.S. Cl. .................... 623/17.12; 623/17.15

(58) Field of Classification Search ........... 623/17.11, 623/17.12, 17.13, 17.14, 17.15, 17.16
See application file for complete search history.

(56) References Cited

U.S. PATENT DOCUMENTS

| | | | | |
|---|---|---|---|---|
| 4,309,777 | A | 1/1982 | Patil | 623/17.13 |
| 4,759,769 | A | 7/1988 | Hedman et al. | 623/17.13 |
| 5,002,576 | A | 3/1991 | Fuhrmann et al. | 623/17.15 |
| 5,389,107 | A | 2/1995 | Nassar et al. | 623/23 |
| 5,458,642 | A | 10/1995 | Beer et al. | 623/17.13 |
| 5,466,261 | A * | 11/1995 | Richelsoph | 623/23.47 |
| 5,676,702 | A | 10/1997 | Ratron | 623/17.16 |
| 5,865,846 | A | 2/1999 | Bryan et al. | 128/898 |
| 5,893,889 | A * | 4/1999 | Harrington | 623/17.16 |
| 5,989,291 | A | 11/1999 | Ralph et al. | 623/17.15 |
| 6,001,130 | A | 12/1999 | Bryan et al. | 623/17.16 |
| 6,022,376 | A | 2/2000 | Assell et al. | 623/17.16 |
| 6,063,121 | A * | 5/2000 | Xavier et al. | 623/17.15 |
| 6,136,031 | A | 10/2000 | Middleton | 623/17.16 |
| 6,156,067 | A | 12/2000 | Bryan et al. | 623/17.15 |
| 6,296,664 | B1 | 10/2001 | Middleton | 623/17.15 |
| 6,315,797 | B1 | 11/2001 | Middleton | 623/17.16 |
| 6,395,032 | B1 * | 5/2002 | Gauchet | 623/17.12 |
| 6,508,841 | B1 | 1/2003 | Martin et al. | 623/23.12 |
| 6,520,996 | B1 | 2/2003 | Manasas et al. | 623/23.5 |
| 6,527,806 | B1 | 3/2003 | Ralph et al. | 623/17.16 |
| 2003/0040800 | A1 * | 2/2003 | Li et al. | 623/17.12 |
| 2003/0135277 | A1 * | 7/2003 | Bryan et al. | 623/17.12 |
| 2003/0135278 | A1 * | 7/2003 | Eckman | 623/17.14 |
| 2003/0199982 | A1 * | 10/2003 | Bryan | 623/17.16 |

FOREIGN PATENT DOCUMENTS

| | | |
|---|---|---|
| WO | WO 00/59412 | 10/2000 |
| WO | WO 00/64385 | 11/2000 |

* cited by examiner

*Primary Examiner*—Bruce E. Snow
(74) *Attorney, Agent, or Firm*—Gifford, Krass, Groh, Sprinkle, Anderson & Citkowski, PC

(57) ABSTRACT

One or more rigid components associated with an articulating bone are used to encase, encapsulate, contain, or otherwise protect a compressible/resilient member. The embodiments are applicable not only to artificial disc replacement (ADR) devices, but also to joint situations including total knee and hip arthroplasty. The cushion elements in the preferred embodiments include synthetic rubbers, hydrogels, elastomers, and other polymeric materials such as viscoelastic polymers and foam polyurethanes. The invention effectively combines the advantages of such materials (cushioning, shape memory, and expansion after insertion in the case of hydrogels), while providing increased protection, particularly the elimination of shear stresses. When applied to an ADR, the invention also minimizes the risk of extrusion.

8 Claims, 10 Drawing Sheets

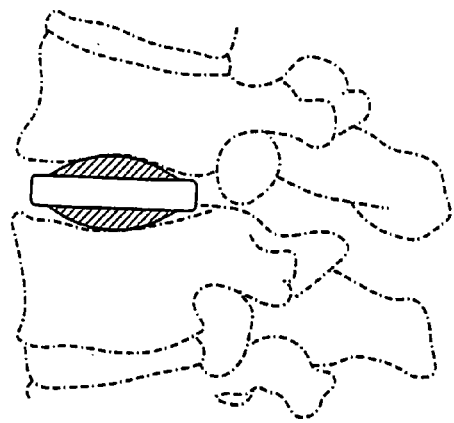
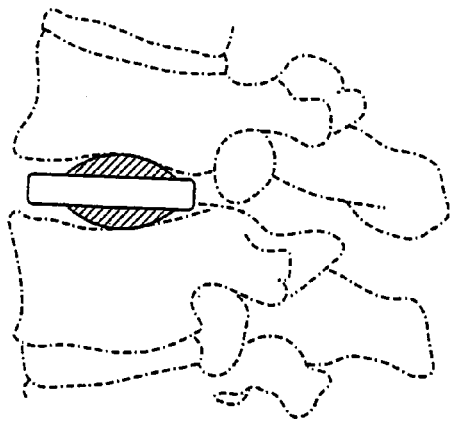
Fig - 2A  Fig - 2B
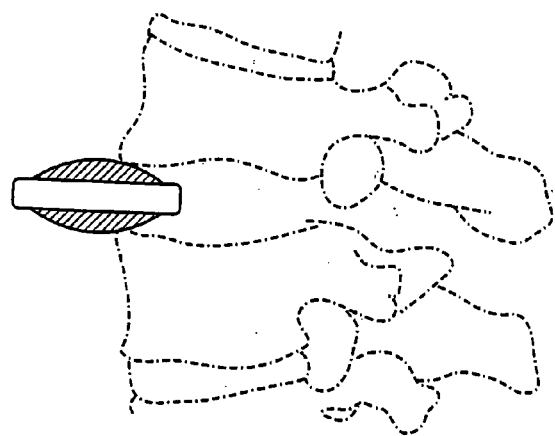
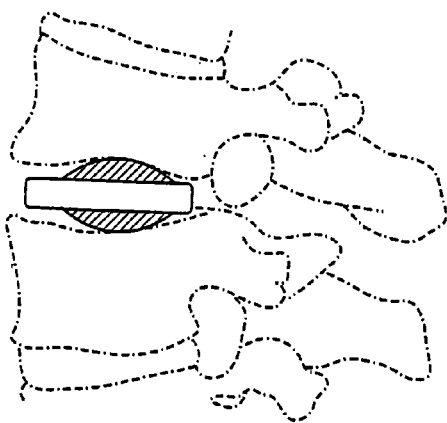
Fig - 3A  Fig - 3B
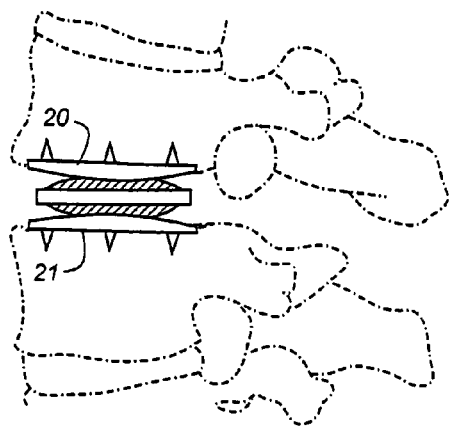
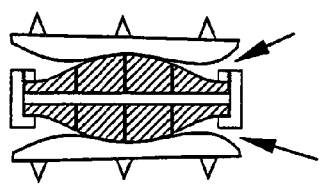
Fig - 4B
Fig - 4A

-OR-

PROSTHETIC COMPONENTS WITH PARTIALLY CONTAINED COMPRESSIBLE RESILIENT MEMBERS

REFERENCE TO RELATED APPLICATION

This application claims priority from U.S. Provisional Patent Application Ser. No. 60/379,462, filed May 10, 2002, and is a continuation-in-part of U.S. patent application Ser. No. 10/422,282, filed Apr. 24, 2003. The content of each application is incorporated herein by reference in their entirety.

FIELD OF THE INVENTION

This invention relates generally to prosthetic implants and, more particularly, to devices of this type including contained, compressible, resilient members.

BACKGROUND OF THE INVENTION

Artificial disc replacements (ADRs) are frequently made of hydrogels or metal and rubber. Hydrogel ADRs generally surround the hydrogel core with a flexible constraining jacket, as shown in PCT/USOO/80920, WO 00/59412.

Unfortunately, the flexibility of the hydrogel and the constraining jacket allow hydrogel ADRs to change shape and extrude through defects in the annulus through which the ADR was inserted, for example. Metal and rubber ADRs often fail at the metal-rubber interface. The rubber fails with the high shear stresses or the rubber separates from the metal with shear stress.

There does exist issued patents that relate to enclosing or sealing hydrogel materials. Of interest is U.S. Pat. No. 6,022,376, which teaches a hydrogel enclosed by a fluid permeable bag. However, the fluid bag does little to protect the hydrogel from shear stress, and the rough texture of the bag may cause hydrogel wear from friction.

U.S. Pat. No. 5,002,576 teaches an elastomer enclosed by rigid cover plates and a corrugated tube. The elastomer is sealed from fluids of the body. The corrugated tube allows movement of the cover plates. The corrugated tube may reduce shear forces on the elastomer. U.S. Pat. Nos. 5,865,846; 6,001,130; and 6,156,067 teach a spherical articulation between ADR EPs and an elastomer. The elastomer may be sealed within the ADR EPs. An annular gasket may reduce shear forces on the elastomer. U.S. Pat. No 5,893,889 teaches an elastomer that is sealed between ADR EPs. The device uses a ball and socket feature to reduce shear on the elastomer. U.S. Pat. No. 6,063,121 incorporates X-shaped wires into the '889 device to reduce rotation.

SUMMARY OF THE INVENTION

In broad and general terms, this invention encases, encapsulates, contains, or otherwise protects a compressible/resilient member with one or more rigid components associated with an articulating bone. The embodiments are applicable not only to artificial disc replacement (ADR) devices, but also to joint situations including total knee and hip arthroplasty. The cushion elements in the preferred embodiments include synthetic rubbers, hydrogels, elastomers, and other polymeric materials such as viscoelastic polymers and foam polyurethanes. The invention effectively combines the advantages of such materials (cushioning, shape memory, and expansion after insertion in the case of hydrogels), while providing increased protection, particularly the elimination of shear stresses. When applied to an ADR, the invention also minimizes the risk of extrusion.

The container that surrounds the cushion element may perform multiple advantageous functions, including:
A. Holds the cushion in place.
B. Reduces frictional forces on the cushion element.
C. Reduces shear forces on the cushion element.
D. In some embodiments, seals the cushion element from exposure to the fluids of the body. Body fluids may destroy the cushion element.
E. In some embodiments, retains particle debris.
F. Prevents the growth of tissues into the ADR. Tissue ingrowth may limit the motion of ADRs.

One disclosed ADR-related embodiment incorporates a polymer cushion element, including elastomers and hydrogels, surrounded by a rigid component or rigid components, to accommodate repeated compression of the cushion element by movement of the rigid component or between the rigid components. This system is may be achieved with or without ADR endplates.

According to a different preferred embodiment, an ADR encloses a polymer cushion element, including elastomers and hydrogels, in a single somewhat flexible metal or plastic component. Alternatively, an ADR with a modular cushion element can be replaced through a removable portion of an outer surrounding component. The surrounding component itself can also be removable. Another ADR according to the invention uses thin rigid liners over elastomer to reduce the friction between the elastomer and ADR EPs. A different embodiment incorporates a novel, motion-limiting keel.

Elastomers, or other polymers, may be provided with caps to reduce friction and wear on the polymer. More than two disc spacer ADRs (ADR without endplates) may be interconnected; more than one polyurethane component may be present in an ADR, and more than two components may interact to limit axial rotation.

BRIEF DESCRIPTION OF THE DRAWINGS

FIG. 2A shows an ADR according to the present invention disposed symmetrically between adjacent vertebrae;

FIG. 2B illustrates an asymmetrical configuration;

FIG. 3A illustrates a device dehydrated for insertion between the vertebrae;

FIG. 3B illustrates the device expanded after insertion and hydration;

FIG. 4A shows the device of the present invention with endplates in position;

FIG. 4B is a cross-section of FIG. 4A;

DETAILED DESCRIPTION OF THE INVENTION

This invention addresses and solves problems associated with artificial disc replacement (ADR) devices and joint-related components, including those associated with total-knee and hip arthroplasty, by effectively combining the advantages of hydrogels and other compressible/resilient materials while minimizing shear stresses. When applied to an ADR, the invention also minimizes the risk of extrusion.

Hydrogels are used in the preferred embodiments. U.S. Pat. Nos. 5,047,055 and 5,192,326, both incorporated by reference, list some of the applicable hydrogels. The small size of the desiccated hydrogel facilitates insertion, after which the hydrogel imbibes fluids and expands. Other non-hydrogel compressible and/or resilient materials may alternatively be used, including elastomers, shape-memory polymers, which would increase in height after they are inserted. As another example of many, non-hydrogel polymers such as acrylics may be used which change shape with a change in temperature. Thus, as used herein, the term "hydrogel" should be taken to include other resilient/compressible materials.

According to the invention, the hydrogels are protected from shear stress, thereby extending longevity. In particular, the hydrogel is contained, constrained or enclosed within a cavity or cylinder which may include one or more pistons. The hydrogel provides cushioning, while the metal pistons facilitate articulate either directly or indirectly with bone surfaces. Thus, the invention offers the advantages of metal-on-metal while providing for cushioning. The hydrogels allow for physiologic tension adjustment since they can change size based upon imbibing fluid and the pressure on the hydrogel. Thus, the hydrogel component of the device can change height to balance the forces against the surrounding tissues.

The cylinder and piston would likely be made of metal such as stainless steel, titanium, chrome cobalt, or other biocompatible metal or ceramic alloy. Surfaces to promote bone ingrowth could be used on the covers. The hydrogel embodiments may incorporate channels for the diffusion of fluids in and out of the cylinder. Optional permeable membranes can also be used to prevent extrusion of the hydrogel through the channels. The permeable membrane traps the hydrogel but allows fluids to move freely across the membrane.

Figure 1A:
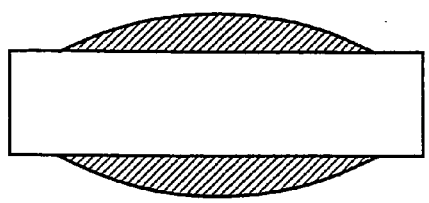
FIG. 1A is a side view of a contained artificial disc replacement (ADR) of the present invention.
Figure 1B:
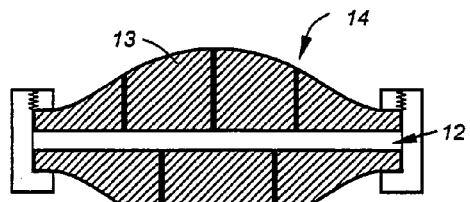
FIG. 1B shows the cross-section of the device of FIG. 1A.
Figure 1C:
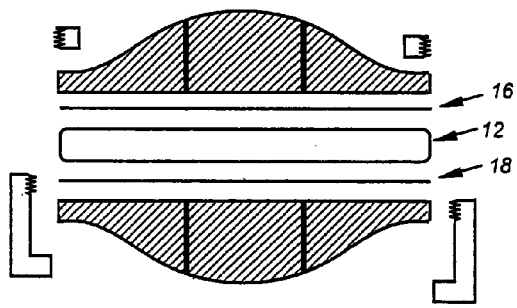
FIG. 1C is an exploded view of the device of FIGS. 1A and 1B.
Figure 1E:
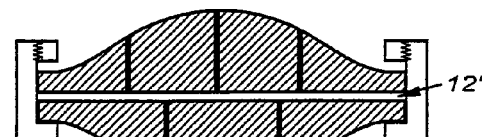
FIG. 1E shows the device in a dehydrated state.
Figure 1D:
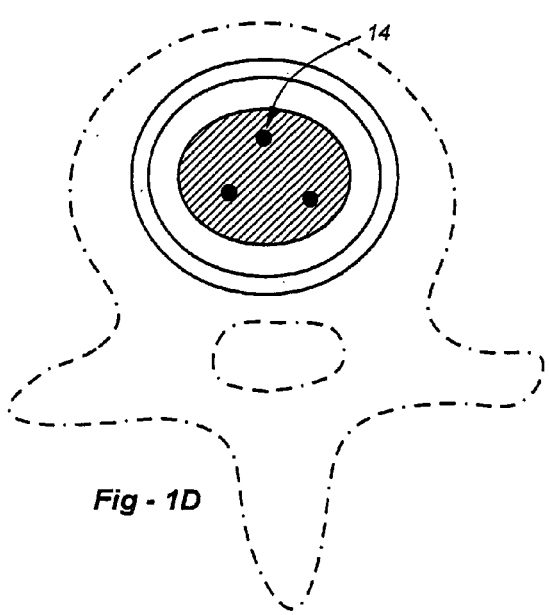
FIG. 1D is a top view of FIGS. 1A–1C in position between a pair of adjacent vertebrae.
Figure 1F:
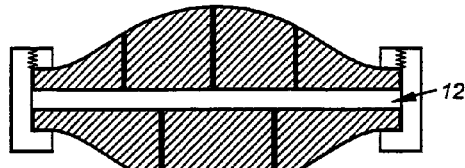
FIG. 1F shows the device in a hydrated/expanded state.

FIG. 1A is a side view of a contained artificial disc replacement (ADR) according to the invention. FIG. 1B is a drawing that shows cross-section of the device of FIG. 1A. Channels through body 13 for fluid migration are shown at 14, and the hydrogel filled chamber is shown at 12. FIG. 1C is an exploded view of the device of FIGS. 1A and 1B. Optional water-permeable membranes are shown at 16 and 18, and the hydrogel layer is shown at 12. FIG. 1D is a top view of FIGS. 1A–1C in position between a pair of adjacent vertebrae. Item 14 shows one of the channels. FIG. 1E shows the device in a dehydrated state, with a narrow space shown at 12'. FIG. 1F shows the device in a hydrated/expanded state with the space 12 expanded after the hydrogel has imbibed fluid.

Devices according to the invention, regardless of disposition in the body, may be placed symmetrically or asymmetrically. FIG. 2A shows an ADR according to the invention disposed symmetrically between adjacent vertebrae. FIG. 2B illustrates an asymmetrical configuration. FIG. 3A illustrates a device dehydrated for insertion between the vertebrae and FIG. 3B illustrates the device expanded after insertion and hydration. As shown in FIG. 4, endplate covers may be provided in conjunction with the contained hydrogel ADR according to the invention. FIG. 4A shows the device and endplates in position. FIG. 4B is a cross-section with the arrows showing the articulated surfaces.

Figure 5A:
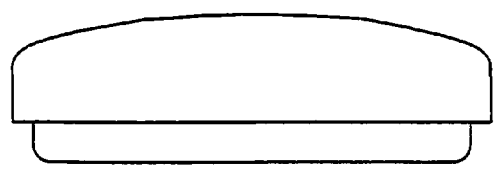
FIG. 5A is a simplified side view of an alternative embodiment of an ADR.
Figure 5B:
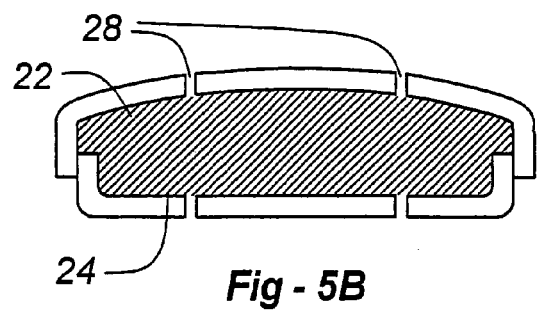
FIG. 5B shows a cross-section of the more encapsulated device showing channels for facilitate fluid transfer.
Figure 5C:
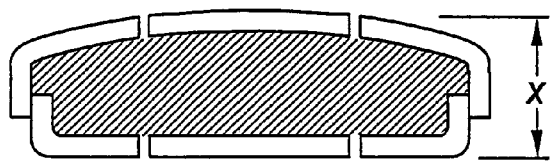
FIG. 5C is a cross-section showing the hydrogel in a desiccated state.
Figure 5D:
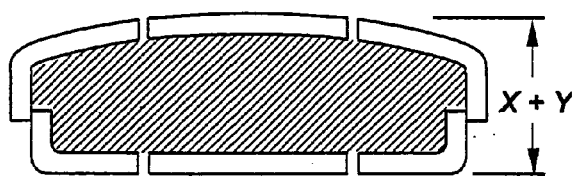
FIG. 5D is a cross-section showing the hydrogel in a hydrated, expanded form.
Figure 5E:
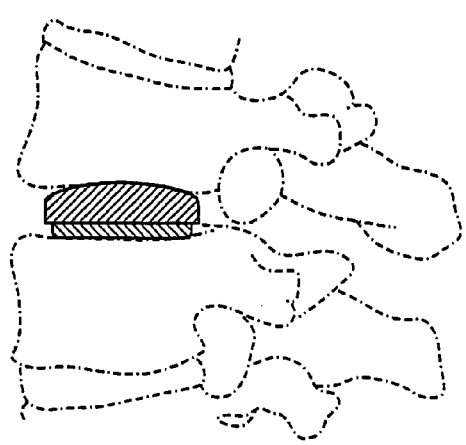
FIG. 5E shows the side view of the device in place between upper and lower vertebrae.
Figure 5F:
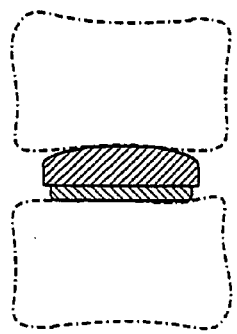
FIG. 5F is an anterior-posterior view of the device in place.
Figure 6A:
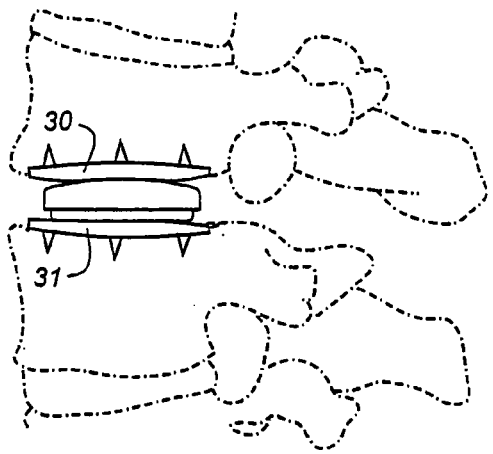
FIG. 6A is a side-view of the device of FIG. 5A with inferior and superior end plates attached to the respective vertebrae.
Figure 6B:
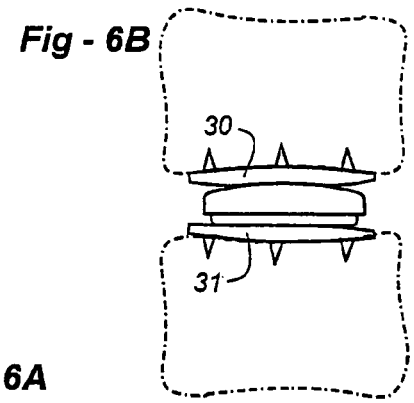
FIG. 6B is an anterior-posterior view of the device of FIG. 6A in position.

FIG. 5A is a simplified side view of an alternative ADR according to the invention, wherein the hydrogel is further encapsulated. FIG. 5B is a cross-section of the more encapsulated device showing channels 28 to facilitate fluid transfer, and a hydrogel 22 and fluid permeable membrane is shown at 24. FIG. 5C is a cross-section showing the hydrogel in a desiccated state having a height "x." FIG. 5D is a cross-section showing the hydrogel in a hydrated, expanded having a height "x+y." FIG. 5E shows the device in place between upper and lower vertebrae from a side view. FIG. 5F is an A-P of the device in place. FIG. 6A is a side-view of the device of FIG. 5, with inferior and superior end plates 30, 31 attached to the respective vertebrae. FIG. 6B is an A-P view of the device of FIG. 6A in position.

Figure 7A:
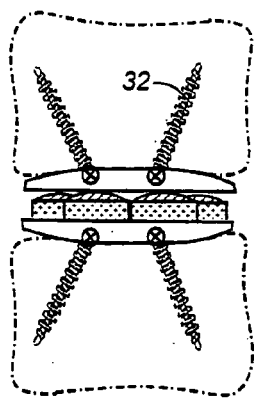
FIG. 7A is an anterior-posterior view of in partial cross-section of an ADR incorporating multiple cylinders.
Figure 7B:
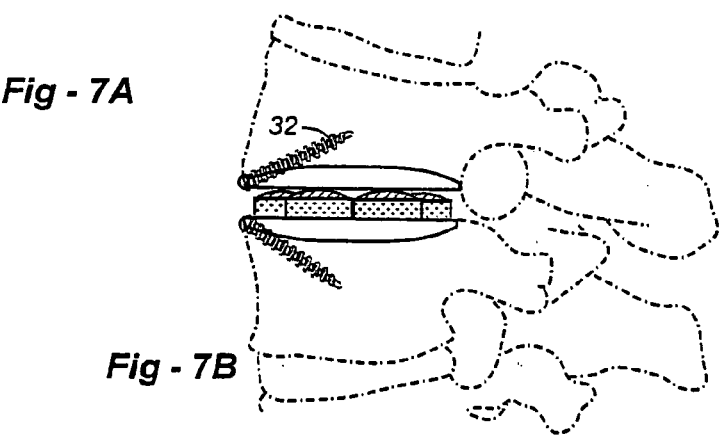
FIG. 7B is a side-view, also in partial cross-section.
Figure 7C:
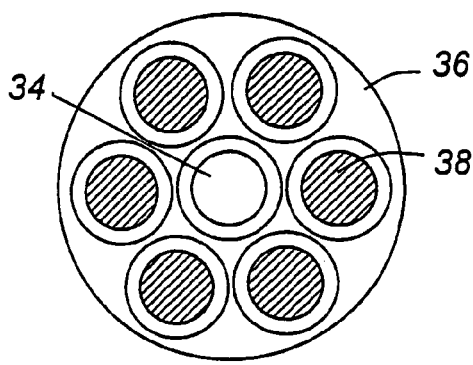
FIG. 7C is an axial cross-section of a device containing a central guide cylinder surrounding six pistons.

The invention may also include two or more cylinders. Adding cylinders reduces the tendency of a single assembly to tilt when pressure is applied in an eccentric fashion. FIG. 7A is an A-P view of in partial cross-section of an ADR incorporating multiple cylinders and end plates attached with screws 32. FIG. 7B is a side-view, also in partial cross-section. FIG. 7C is an axial cross-section of a device containing a metal-ceramic hydrogel cylinder 36, and a central guide cylinder 34 surrounding six pistons 38. It will be appreciated that more or fewer guide cylinders and/or pistons may be used as shown, for example, in FIG. 10.

Figure 7D:
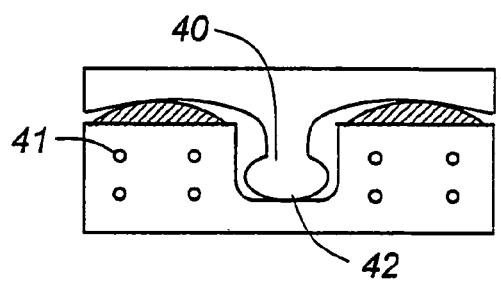
FIG. 7D shows two embodiments with multiple cylinders.
Figure 7D:
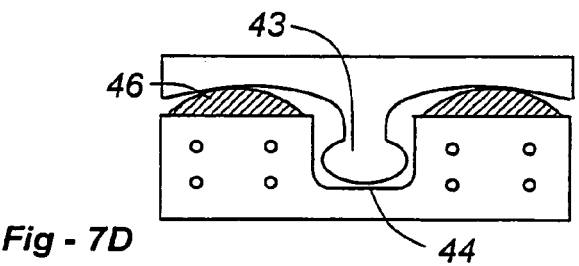

FIG. 7D shows two embodiments with multiple cylinders. In the partial cushion embodiment (upper drawing), the spherical end 42 of the peg 40 projecting from the top plate rests against and is partially supported by a concavity in the lower plate. Holes for fluid transfer are shown at 41. In the full cushion embodiment (lower drawing), the peg projecting from the top plate 43 fits into a restraining cylinder 44. The peg form the top plate does not rest against the bottom plate in this embodiment. A piston is depicted at 46. In either case, the end of the peg is preferably spherical to allow angular motion between the two plates.

Figure 8A:
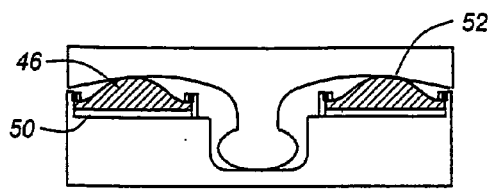
FIG. 8A is a coronal/sagittal cross-section of the cylinders according to the present invention.
Figure 8B:
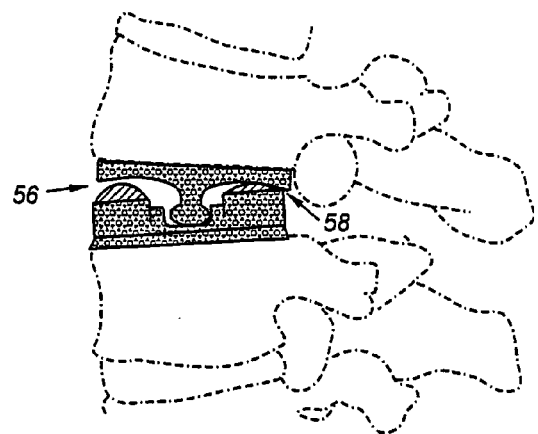
FIG. 8B is an illustration of two vertebrae in extension.
Figure 9:
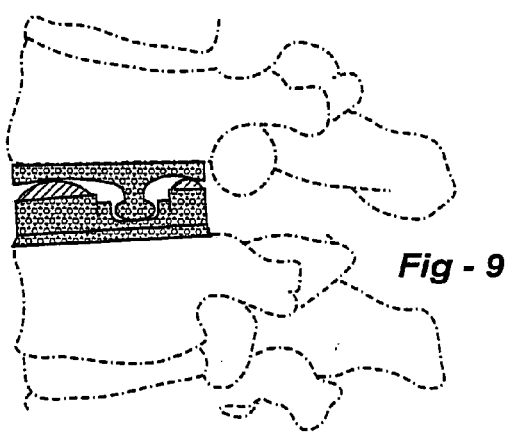
FIG. 9 shows an embodiment with the peg projecting from the posterior aspect of the inferior surface of the upper plate.

FIG. 8A is a coronal/sagittal cross-section of the cylinders according to this embodiment of the invention. A top plate 52 has concavities opposite the piston 46, and the hydrogel layer is shown at 50. FIG. 8B is an illustration of two vertebrae in extension, showing the way in which the front piston is raised 56 and the back piston is lowered 58. Note that the peg that projects from the lower portion of the upper plate need not be central in location. FIG. 9 shows an embodiment with the peg projecting from the posterior aspect of the inferior surface of the upper plate. Posterior peg placement allows a larger anterior cylinder. The larger anterior cylinder may be better at handling the larger forces placed on the anterior portion of the disc replacement during spinal flexion.

Figure 10B:
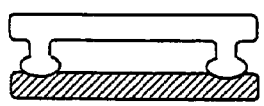
FIG. 10B is a frontal view in cross-section showing partial cushioning.
Figure 10C:
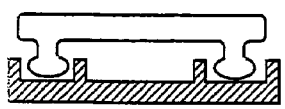
FIG. 10C is a frontal cross-sectional view illustrating full cushioning.
Figure 10A:
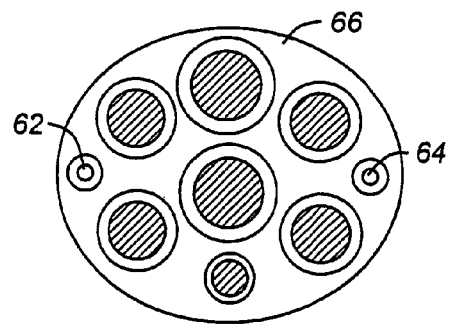
FIG. 10A shows a further alternative embodiment of the present invention.
Figure 11B:
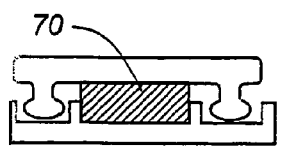
FIG. 11B is a side-view drawing in cross-section showing partial cushioning of the device of FIG. 11A.
Figure 11C:
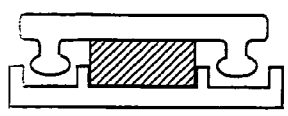
FIG. 11C is a side-view drawing in partial cross-section illustrating the embodiment of FIGS. 11A and 11B.
Figure 11A:
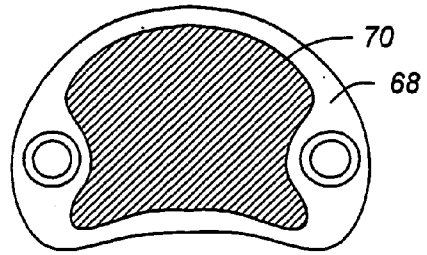
FIG. 11A is a top-down view of an embodiment showing opposing retaining cylinders on either side of a central resilient member.

FIG. 10 is a drawing which shows an alternative arrangement wherein multiple guide cylinders are used at the periphery as opposed to a central location. Among other advantages, this may help to prevent rotatory subluxation of the top component relative to the bottom component while allowing more area centrally for the hydrogels/polymer cylinders. FIG. 10A is a top cross-section view of an embodiment showing multiple peripheral cylinders in a housing 66, additional internal hydrogel chambers, and guides cylinders 62, 64. FIG. 10B is a frontal view in cross-section showing partial cushioning. FIG. 10C is a frontal cross-sectional view illustrating full cushioning. Two or more retaining cylinders may also be used to reduce the shear on the solid piece of silicone rubber, elastomer or hydrogel-type material. FIG. 11A is a top-down view of an embodiment 68 showing opposing retaining cylinders on either side of a central resilient member 70. FIG. 11B is a side-view drawing in cross-section showing partial cushioning of the device of FIG. 11A with an elastomer spacer 70. FIG. 11C is a side-view drawing in partial cross-section illustrating the embodiment of FIGS. 11A and 11B providing a full cushioning and reduced shear capability.

Figure 12A:
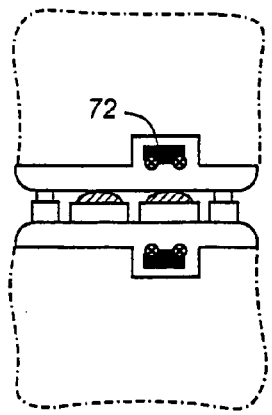
FIG. 12A shows an anterior-posterior view of the embodiment of the invention wherein the end plates of ADR may contain hollow keels on the vertebral side.
Figure 12B:
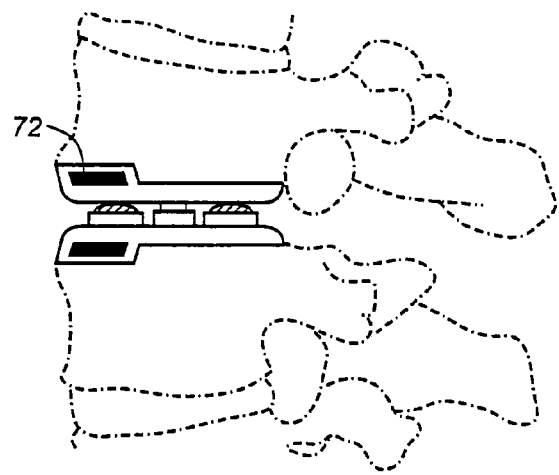
FIG. 12B is a lateral view of FIG. 12A.
Figure 12C:
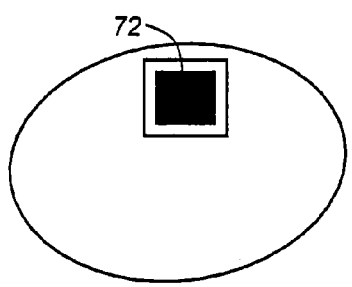
FIG. 12C is a top-down view illustrating the bone ingrowth area of FIG. 12A.

Reference is now made to FIG. 12A, which is an A-P view of the embodiment of the invention wherein the end plates of ADR may contain hollow keels on the vertebral side. FIG. 12B is a lateral view and, FIG. 12C is a top-down view illustrating the bone ingrowth area 72. The vertebrae would be osteotomized to make room for the keels. The bone from the osteomity sites would be morselized and placed inside the hollow keels. The morselized bone would promote ingrowth into the end plates of the ADR, much like hollow cages promote bone ingrowth.

Figure 13:
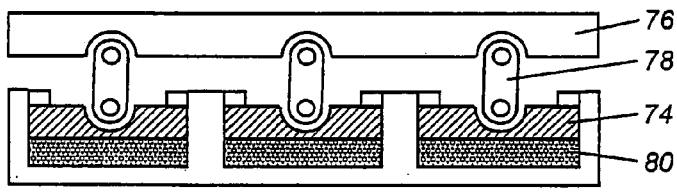
FIG. 13 is a cross-section of an embodiment with multiple pistons connected to the top plate via a rod.
Figure 14A:
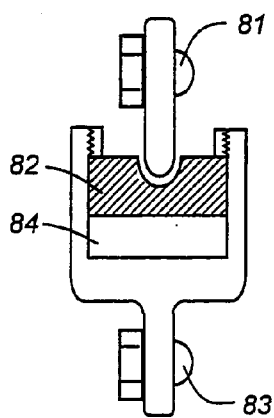
FIG. 14A is a cross-section illustrating an anterior-posterior view of two pedicle screws.
Figure 14B:
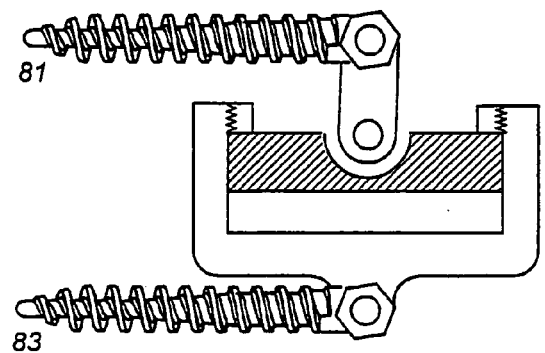
FIG. 14B is a cross-sectional lateral view of the embodiment of FIG. 14A.
Figure 15A:
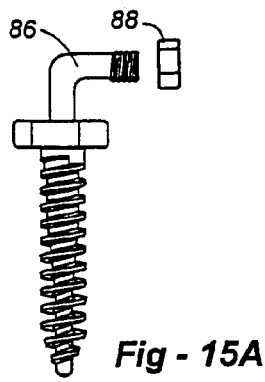
FIG. 15A is a side-view of a pedicle screw having an axle to receive a shock absorber according to the present invention.
Figure 15B:
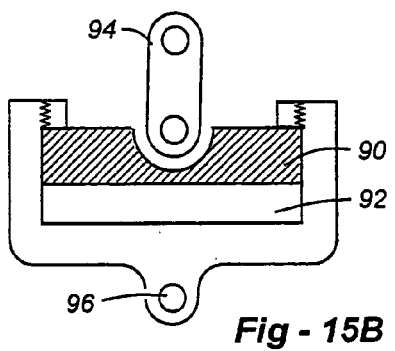
FIG. 15B is a close-up of the shock absorber mechanism associated with a pedicle screw embodiment of FIG. 15A.

FIG. 13 is a cross-section of an embodiment with multiple pistons 74 connected to the top plate via rod 78 that swivels between top endplate 76 and piston 74, much like the design of rods that connect pistons to a crankshaft in an engine. The layer below the pistons is a hydrogel 80. The shock absorber concept according to this invention may also be used with respect to vertebral shock absorbers. FIG. 14A is a cross-section illustrating an A-P view of two pedicle screws 81, 83 coupled in this way. The layer below the pistons 82 is a hydrogel 84. FIG. 14B is a cross-sectional lateral view of the embodiment of FIG. 14A showing screws 81, 83. FIG. 15A is a side-view of a pedicle screw having an axle 86 and nut 88 to receive a shock absorber according to the invention. FIG. 15B is a close-up of the shock absorber mechanism associated with a pedicle screw embodiment. Holes for attachement 94 and 96 are shown with a piston 90 and a hydrogel layer 92.

The cylinders could be made of ceramic, metal, or metal lined with ceramic. The pistons could also be made of metal, ceramic, alloys and so forth. In any case, the articulation of the top and bottom plates is preferably metal-to-metal or ceramic-to-metal, both of which are presumably superior to metal-to-polyethylene articulations. Furthermore, hydrogels, shape memory polymers, or other polymers within the cylinder provide a cushion, or dampen the forces across the plates.

Polymers of different durometers could be used in cylinders in different locations. For example, the polymers in the posterior cylinders could be less compressible and therefore help resist extension of the spine. The cylinders could also use liquids with baffles to dampen motion. That said, hydrogels or polymers have the benefit of functioning without a water tight cylinder piston unit. Indeed, as mentioned previously, the cylinders or the pistons may contain holes to allow fluid movement in the hydrogel configurations.

As discussed above, this invention is not limited to the spine, but may be used in other joint situations such as the knee and hip, which typically use polyethylene bearing surfaces on the acetabulum or proximal tibia. Problems related to polyethylene wear are well known to orthopedic surgeons. Although metal-on-metal and ceramic-on-ceramic total hips have been developed to reduce the problems associated with poly wear, such designs do not provide shock-absorbing capacity. For example, excessive force form tight ligaments about the knee or hip may reduce the size of the hydrogel, thus reducing the tension on the ligaments. Conversely, loose ligaments will cause the hydrogel to swell, thus increasing the tension on the loose ligaments. Although hydrogels are used in this preferred embodiment as well, other elastomers and polymers including shape memory polymers may alternatively be used.

Figure 16:
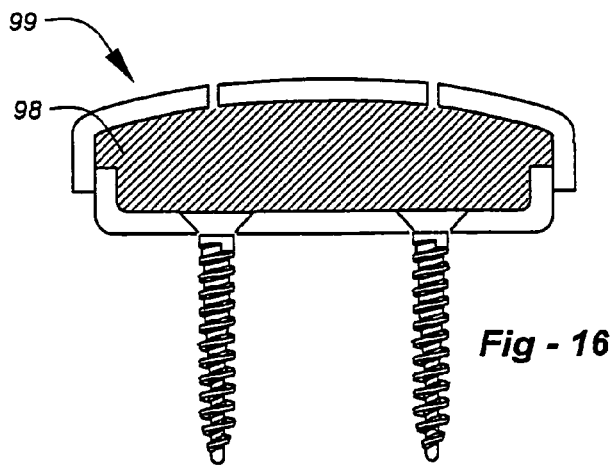
FIG. 16 is a cross-sectional view of a tibial component according to the present invention.
Figure 17:
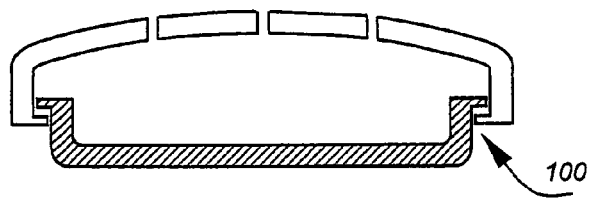
FIG. 17 is a drawing which shows how a locking component may be incorporated in the design.
Figure 18:
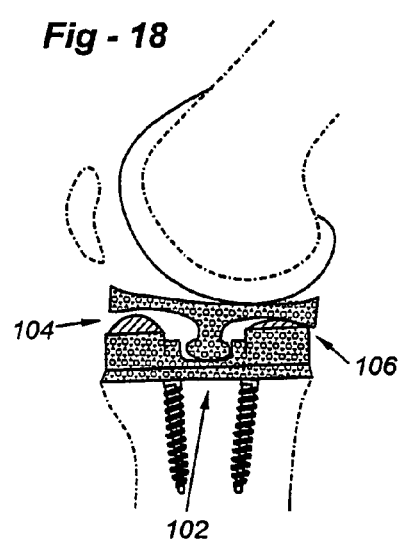
FIG. 18 is a side-view cross-section of a tibial component for a knee replacement.

FIG. 16 is a cross-sectional view of a tibial component according to the invention shown generally at 99. As discussed above, channels are used for fluid transfer, and these may be located around the periphery, or near the center, rather than in the weight-bearing area. Item 98 shows the resilient, fluid-imbibing center. FIG. 17 is a drawing which shows how a locking component 100 may be incorporated in the design which allows movement while, at the same time, prevent disassociation. A similar design may be used for other prosthetic components, including a patella button. FIG. 18 is a side-view cross-section of a tibial component 102 for a knee replacement utilizing a central guide and peripheral pistons, showing the way in which the front piston is raised 104 and the back piston is lowered 106, much like the vertebral embodiments discussed with reference to FIGS. 7–11, in particular.

Figure 19:
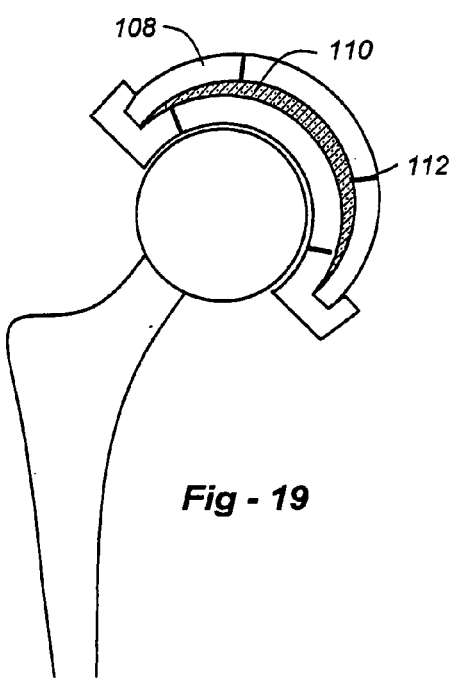
FIG. 19 is a side-view drawing of an embodiment illustrating the way in which the invention may be applied to the hip.

FIG. 19 is a side-view drawing of an embodiment illustrating the way in which the invention may be applied to the hip. As shown in the drawing, an inner cup 108 would be used with respect to the acetabulum, along with an outer bearing surface with a hydrogel/elastomeric or other polymeric material 110 being used therebetween. Particularly with regard to a hydrogel configuration, one or more channels 112 for fluid transfer may be provided.

Figure 20:
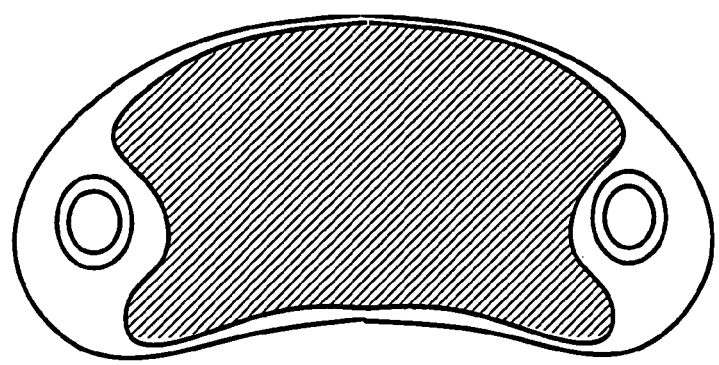
FIG. 20 is a view of the top of an alternative embodiment of the ADR drawn in FIG. 11A.

FIG. 20 is a view of the top of an alternative embodiment of the ADR drawn in FIG. 11A. The cylinders that cooperate with the pistons are elongated to allow translation. Alternatively, the cylinders could have a central torodial region to allow translation.

Figure 21A:
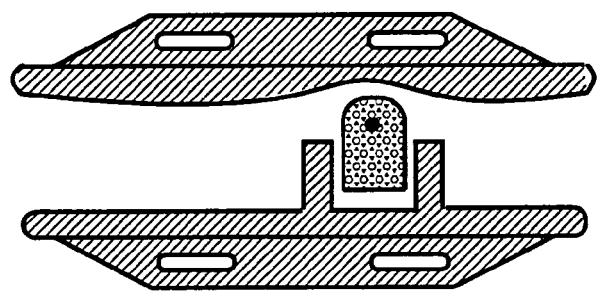
FIG. 21A is a sagittal cross section through an alternative embodiment of the ADR drawn in FIG. 13.

FIG. 21A is a sagittal cross section through an alternative embodiment of the ADR drawn in FIG. 13. One or more pistons are connected to the upper ADR EP by an axle or axles. The hinged pistons facilitate ADR flexion and extension. A loose fit between the piston and the cylinder would permit a few degrees of lateral bending. A single piston embodiment allows unlimited axial rotation. The piston or pistons can be located centrally or in non-central locations. For example, the piston could be located in the posterior half of the ADR.

Figure 21B:
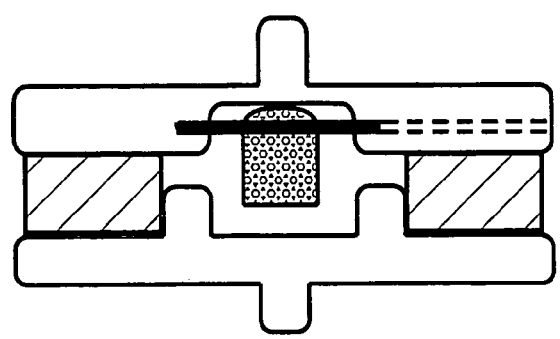
FIG. 21B is a coronal cross section of the embodiment of the ADR drawn in FIG. 21A.

FIG. 21B is a coronal cross section of the embodiment of the ADR drawn in FIG. 21A.

Figure 22A:
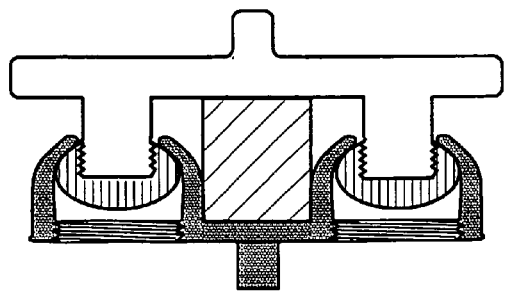
FIG. 22A is a coronal cross section of a constrained embodiment of the ADR shown in FIG. 11.

FIG. 22A is a coronal cross section of a constrained embodiment of the ADR drawn in FIG. 11. The balls on the pistons will not fit through the openings in the cylinders of the ADR.

Figure 22B:
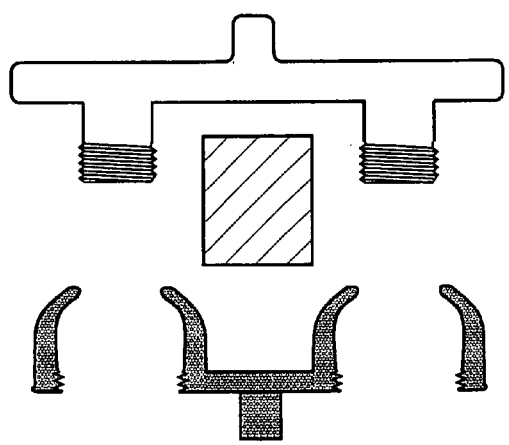
FIG. 22B is an exploded anterior view of the ADR shown in FIG. 22A.

FIG. 22B is an exploded anterior view of the ADR drawn in FIG. 22A. The balls for the pistons are threaded onto the pistons through openings on the bottom of the inferior ADR EP. Screws can be used to close the openings in the inferior ADR EP.

Figure 23:
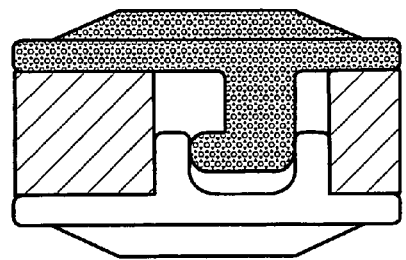
FIG. 23 is a sagittal cross section of an alternative embodiment of the ADR shown in FIG. 11.

FIG. 23 is a sagittal cross section of an alternative embodiment of the ADR drawn in FIG. 11. The shaft of the piston is located eccentrically on the ball at the end of the piston. The shaft of the piston selectively impinges with the walls of the cylinder to limit ADR motion. For example, the impingement could limit ADR extension.

Figure 24:
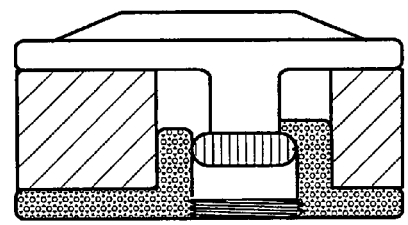
FIG. 24 is a sagittal cross section of an alternative embodiment of the ADR drawn in FIG. 22.

FIG. 24 is a sagittal cross section of an alternative embodiment of the ADR drawn in FIG. 22. The shaft of the piston selectively impinges on a projection from the walls of the cylinder to limit ADR motion. For example, the impingement could limit ADR extension.

Figure 25:
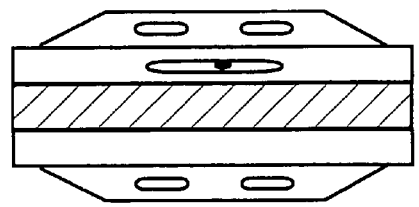
FIG. 25 is a lateral view of an alternative embodiment of the ADR drawn in FIG. 21A.

FIG. 25 is a lateral view of an alternative embodiment of the ADR drawn in FIG. 21A. A slot allows the axle to translate forward and backward. Translation of the axle permits translation of the ADR EPs.

Figure 26A:
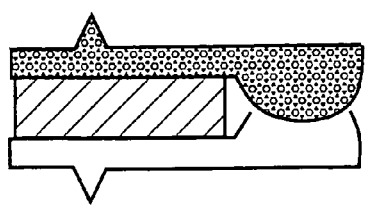
FIG. 26A is a sagittal cross section of an alternative embodiment of the ADR.
Figure 26B:
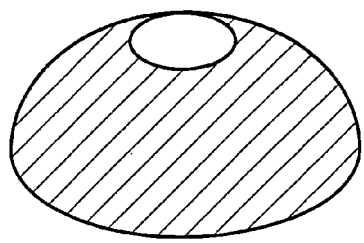
FIG. 26B is a view of the top of the elastomeric component and the socket of the inferior ADR EP drawn in FIG. 26A.

FIG. 26A is a sagittal cross section of an alternative embodiment of the ADR. A ball and socket joint is located in the posterior aspect of the ADR. A cushion element is located anterior to the ball and socket joint. The cushion element could be made of polymers or springs. FIG. 26B is a view of the top of the elastomeric component and the socket of the inferior ADR EP drawn in FIG. 26A.

Figure 27:
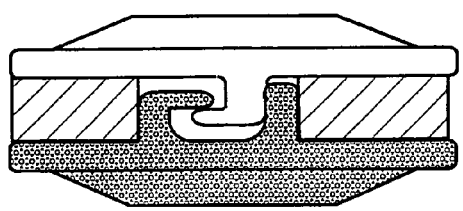
FIG. 27 is a sagittal cross section of an alternative embodiment of the ADR.

FIG. 27 is a sagittal cross section of an alternative embodiment of the ADR. The projection from the piston or pistons fit through a slot in the top of the cylinder/cylinders. The two ADR EPs can be rotated after inserting the projection through the slot thus, reversibly locking the ADR EPs together. The projection could also interact with the top of the cylinder to limit ADR motion.

Figure 28B:
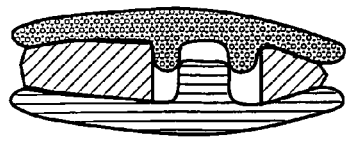
FIG. 28B is a sagittal cross section through another "Disc Spacer" embodiment of the ADR.
Figure 28A:
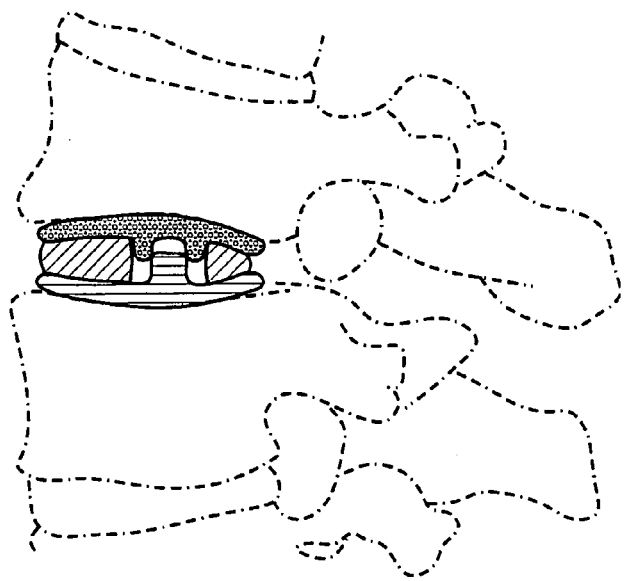
FIG. 28A is a sagittal cross section of the spine and an alternative embodiment of the device.

FIG. 28A is a sagittal cross section of the spine and an alternative embodiment of the device. The piston and cylinder containing members articulate with the vertebral endplates, they are not fastened to the endplates of the vertebrae. All of the embodiments drawn in this application could be converted into similar "Disc Spacer" ADRs. Articulation between the components can be located centrally or eccentrically. For example, the articulation may be located in the posterior half of either component or both components. The drawing illustrates a posterior location of the articulation.

Figure 28C:
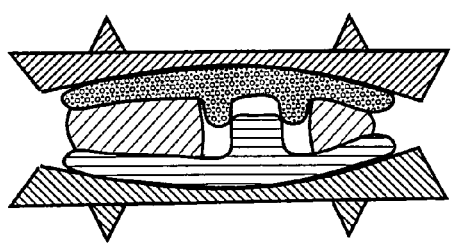
FIG. 28C is a sagittal cross section through another embodiment of the device.
Figure 28D:
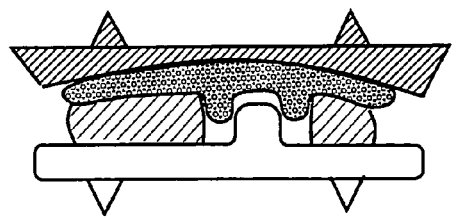
FIG. 28D is a sagittal cross section through another embodiment of the device.

FIG. 28B is a sagittal cross section through another "Disc Spacer" embodiment of the ADR. The end of the piston contains a spherical enlargement. For example, the ball and socket of FIG. 9A shown in co-pending U.S. patent application entitled "Artificial Intervertebral Disc Spacers" can be surrounded by a viscoelastic component. FIG. 28C is a sagittal cross section through another embodiment of the device. The disc spacer articulates with ADR EPs as described the co-pending application discussed above. FIG. 28D is a sagittal cross section through another embodiment of the device. The piston component projects from the inferior ADR EP. The cylinder component articulates with the piston component and a superior ADR EP. This two-articulation embodiment is similar to a "cushioned" embodiment of the two articulation ADRs is also described in the co-pending U.S. patent application referenced above.

The invention claimed is:

1. An artificial disc replacement (ADR), comprising:
   a flattened piston and cylinder adapted for placement between an opposing pair of vertebral bodies;
   the piston having an exposed, articulating top surface, a bottom surface, and an outer sidewall;
   the cylinder having a bottom portion and an inner sidewall dimensioned to receive the outer sidewall of the piston in sliding engagement;
   a cavity within the cylinder between the bottom of the piston and the bottom of the cylinder, the cavity being filled with a hydrogel of the type that imbibes fluid; and
   one or more bidirectional channels into the cavity, allowing the hydrogel to expel fluid when the piston is compressed into the cylinder and take up fluid when the compression is released.

2. The ADR of claim 1, further including a mechanism to limit the relative movement of the endplates.

3. The ADR of claim 1, wherein the articulating top surface of the piston is convex.

4. The ADR of claim 1, wherein the fluid paths are formed through the piston.

5. The ADR of claim 1, wherein the bottom of the cylinder is formed with a second sliding piston, the second piston having an exposed, articulating bottom surface and a top surface in contact with the hydrogel.

6. The ADR of claim 5, wherein the articulating bottom surface of the second piston is convex.

7. The ADR of claim 5, further including an endplate component between the articulating bottom surface of the second piston and a lower vertebral body.

8. The ADR of claim 1, further including an endplate component between the articulating top surface of the piston and an upper vertebral body.

* * * * *